United States Patent [19]
Podolski et al.

[11] Patent Number: 5,965,144
[45] Date of Patent: Oct. 12, 1999

[54] CHITOSAN INDUCED IMMUNOPOTENTIATION

[75] Inventors: Joseph S. Podolski, The Woodlands; Mitzi L. Martinez, Conroe, both of Tex.

[73] Assignee: Zonagen, Inc., The Woodlands, Tex.

[21] Appl. No.: 09/066,227

[22] Filed: Apr. 24, 1998

Related U.S. Application Data

[62] Division of application No. 08/823,143, Mar. 25, 1997.

[51] Int. Cl.$^6$ .......................... A61K 45/00; A01N 43/04
[52] U.S. Cl. .................................... 424/278.1; 424/279.1; 424/283.1; 514/23
[58] Field of Search ............................... 424/93.1, 130.1; 435/7.1; 436/500; 514/1–768; 530/350–507, 817–868

[56] References Cited

U.S. PATENT DOCUMENTS

| | | | |
|---|---|---|---|
| 4,372,883 | 2/1983 | Matsuhashi et al. | 260/112 R |
| 4,801,578 | 1/1989 | Monsigny et al. | 514/8 |
| 4,814,169 | 3/1989 | Matsuhashi et al. | 424/85.8 |
| 4,971,956 | 11/1990 | Suzuki et al. | 514/55 |
| 5,455,032 | 10/1995 | Kenny et al. | 424/194.1 |

FOREIGN PATENT DOCUMENTS

| | | |
|---|---|---|
| 0 183 556 A2 | 6/1987 | European Pat. Off. |
| WO 90/14837 | 12/1990 | WIPO . |
| WO 96/09805 | 4/1996 | WIPO . |
| WO 96/10421 A1 | 4/1998 | WIPO . |

OTHER PUBLICATIONS

Edelman, R., "Vaccine Adjuvants," *Rev. Infect. Dis.,* 2(3):370–383 (May–Jun., 1980).

Freund et al., "Sensitization and Antibody Formation after Infection of Tubercle Bacilli and Paraffin Oil," *Proc. Soc. Exp. Biol. Med.,* 37:509–513 (1937).

Gajewski et al., "Antiproliferative Effect of IFN–γ In Immune Regulation III. Differential Selection of $T_H1$ and $T_H2$ Murine Helper T Lymphocyte Clones Using Recombinant IL–2 and Recombinant IFN–γ," *J. Immunol.,* 143(1):15–22 (Jul. 1, 1989).

Gajewski et al., "Murine Th1 and Th2 Clones Proliferative Optimally in Response to Distinct Antigen–Presenting Cell Populations," *J. Immunol.,* 146(6):1750–1758 (Mar. 15, 1991).

Gery et al., "Stimulation of B–Lymphocytes By Endotoxin: Reactions of Thymus–Deprived Mice and Karyotypic Analysis of Divding Cells in Mice Bearing $T_6T_6$ Thymus Grafts," *J. Immunol.,* 108(4):1088–1091 (Apr. 1972).

Grun et al., "Different T Helper Cell Subsets Elicited in Mice Utilizing Two Different Adjuvant Vehicles: The Role of Endogenous Interleukin 1 in Proliferative Responses," *Cell. Immunol.,* 121:134–145 (1989).

Gupta et al., "Adjuvants–A Balance Between Toxicity and Adjuvanticity," *Vaccine,* 11:291–306 (1993).

Harris et al., "Cloning and Characterization of Zona Pellucida Genes and cDNAs from a Variety of Mammalian Species: The ZPA, ZPB, and ZPC Gene Families," *J. Seq. and Mapping,* 4:361–393 (1994).

Johnson et al., "Studies on the O Antigen of Salmonella Typhosa V. Enhancement of Antibody Response to Protein Antigens by the Purified Lipopolysaccharide," *J. Exp. Med.,* 103:225–246 (1956).

Marcinkiewicz et al., "Immunoadjuvant Properties of Chitosan," *Arch. Immunol. et Ther. Exp.,* 39:127–132 (1991).

Mosmann et al., "TH1 and TH2 Cells: Different Patterns of Lymphokine Secretion Lead to Different Functional Properties," *Ann. Rev. Immunol.,* 7:145–173 (1989).

Nishimura et al., "Immunological Activity of Chitin and Its Derivatives," *Vaccine,* 2:93–99 (1984).

Ramanathan et al., "Complement Activation by Aluminium and Zirconium Compounds," *Immunol.,* 37:881–888 (1979).

Sarin et al., "Cytotoxic and Humoral Immune Responses to HIV–1 p17 Synthetic Peptide HGP–30 in Human Volunteers," *Vaccine Res.,* 3(1):49–57 (1994).

Siskind, G., "Manipulation of the Immune Response," *Pharm. Rev.,* 25(2):319–324 (1973).

Tomai et al., "T Cell and Interferon–γ Involvement in the Adjuvant Action of a Detoxified Endotoxin," *J. Biol. Resp. Mod.,* 8:625–643 (1989).

Warren et al., "Current Status of Immunological Adjuvants," *Ann. Rev. Immunol.* 4:369–388 (1986).

White et al., "Studies on the Antibody Production III. The Alum Granuloma," *J. Exp. Med.,* 102:73–82 (1955).

Wang, G–H, J. Food Prot. 55:11, 916–919 (Nov. 30, 1992).

Immunochemistry in Practice, 2nd ed., Johnstone, A., and Thorpe, R., Yearbook Medical Publishers, 1987.

*Primary Examiner*—Paula K. Hutzell
*Assistant Examiner*—Timothy A. Worrall
*Attorney, Agent, or Firm*—Marshall, O'Toole, Gerstein, Murray & Borun

[57] ABSTRACT

Methods and compositions for potentiating an immune response are disclosed which incorporate chitosan as an immunopotentiating adjuvant. Administration of the compositions of the invention is effected by various routes.

7 Claims, No Drawings

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
         (A) LENGTH: 12 amino acids
         (B) TYPE: amino acid
         (C) STRANDEDNESS: Not Relevant
         (D) TOPOLOGY: linear (ii) MOLECULE TYPE: peptide (xi) SEQUENCE DESCRIPTION: SEQ ID NO:1:

Gly Gln His Lys Pro Glu Ala Pro Asp Tyr Ser Ser
1               5                  10

(2) INFORMATION FOR SEQ ID NO:2:

(i) SEQUENCE CHARACTERISTICS:
         (A) LENGTH: 12 amino acids
         (B) TYPE: amino acid
         (C) STRANDEDNESS: Not Relevant
         (D) TOPOLOGY: linear (ii) MOLECULE TYPE: peptide (xi) SEQUENCE DESCRIPTION: SEQ ID NO:2:

Arg Gly Asp Cys Glu Gly Leu Gly Cys Cys Tyr Ser
1               5                  10

(2) INFORMATION FOR SEQ ID NO:3:

(i) SEQUENCE CHARACTERISTICS:
         (A) LENGTH: 18 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:3:

Ala Pro Asp Thr Asp Trp Cys Asp Ser Ile Pro Ala Arg Asp Arg Leu
1               5                  10                  15
Pro Cys (2) INFORMATION FOR SEQ ID NO:4:

(i) SEQUENCE CHARACTERISTICS:
         (A) LENGTH: 12 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:4:

Asp Arg Ala Val Tyr Glu Asn Glu Leu Val Ala Thr
1               5                  10

(2) INFORMATION FOR SEQ ID NO:5:

(i) SEQUENCE CHARACTERISTICS:
         (A) LENGTH: 12 amino acids
         (B) TYPE: amino acid
         (C) STRANDEDNESS:

-continued (D) TOPOLOGY: linear (ii) MOLECULE TYPE: peptide (xi) SEQUENCE DESCRIPTION: SEQ ID NO:5:

Met Pro Val Gly Val Glu Gly Ala Gly Ala Ala Glu
1               5                   10

(2) INFORMATION FOR SEQ ID NO:6:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Val Ser Ser Lys Gly Pro Met Ile Leu Leu Gln Ala Thr Lys Asp Pro
1               5                   10                  15

Pro Glu Lys Leu Arg Val Pro Val
            20

CHITOSAN INDUCED IMMUNOPOTENTIATION

This is a divisional of U.S. application Ser. No. 08/823,143, filed Mar. 25, 1997.

FIELD OF THE INVENTION

The present invention relates generally to methods for potentiating an immune response in an animal, compositions to effect the potentiation, and methods to produce the compositions. More specifically, the invention provides methods comprising the use of an antigen/chitosan mixture or an antigen/chitosan/oil/surfactant emulsion to potentiate an immune response, antigen/chitosan mixtures or antigen/chitosan/oil/surfactant emulsions to effect potentiation, and methods to prepare the antigen/chitosan mixture or antigen/chitosan/oil emulsion.

BACKGROUND OF THE INVENTION

Recent biotechnological advances have facilitated identification and isolation of components in complex antigens which provide prospects for successful development of safe and practical vaccines. Often, however, these isolated components are not as immunogenic as the complete complex antigens from which they were derived. In order to enhance an immune response to a weakly antigenic immunogen in a recipient animal, adjuvants are frequently administered with the immunogen. Despite the universal acceptance of adjuvants, however, the number suitable for use in humans is limited.

Ideally, an adjuvant should potentiate long-lasting expression of functionally active antibodies, elicit cell-mediated immunity (CMI), and enhance production of memory T- and B-lymphocytes with highly specific immunoreactivity against an invading antigen. In addition to providing a defense upon immediate challenge with an foreign antigen, these responses should provide protection against any future encounters of the host with a specific antigen. More important is the ability of an adjuvant to augment the immune response with a minimum of toxic side effects. Therefore, efficacy of an adjuvant is described in terms of how it balances positive (potentiated immunity) and negative (toxicity) influences.

Controlled immunization for the purpose of stimulating antibody production by B cells is dependent upon a myriad of factors inherent to both the antigen itself and the immunized animal. In general, the farther removed in evolutionary terms the antigen, or its source, is from the invaded host, the more effective the immune response elicited by the antigen. Antigens derived from closely related species are less competent in eliciting antibody production due to the fact that the host immune system is sometimes unable to clearly distinguish the foreign antigen from endogenous, or self antigens. In addition, the dosage of the antigen, the purity of the antigen, and the frequency with which the antigen is administered are also factors which significantly contribute to the resulting antibody titer and specificity of the resulting antibodies. Still other factors include the form, or complexity, of the antigen, and how the antigen is administered. Finally, both the genetic makeup and overall physiological state of the immunized animal contribute to the extent to which an immune response is mounted. Of these factors, the form or complexity of the antigen is directly affected by immunization with an adjuvant.

Current understanding suggests that adjuvants act to augment the immune response by a variety of different mechanisms. In one mechanism, the adjuvant directly stimulates one of either CD4$^+$ helper T-cell subpopulations designated $T_H1$ or $T_H2$ [Mosmann and Coffman, *Ann. Rev. Immunol.* 7:145–173 (1989)]. Helper T cells are required for B-cell antibody responses to most antigens. In an appropriate immune response, an antigen is captured and processed by an antigen-presenting cell (APC), e.g., circulating or tissue macrophages, and presented on the surface of the APC in association with a class II major histocompatibility (MHC) molecule. In this form, the antigen can interact with receptors on the surface of helper T cells thereby activating the particular subpopulation of cells to express and secrete any of a number of cytokines. The nature of cytokine production depends on the subset of helper T cells activated, a result that can be modulated in part by the choice of adjuvant. For example, alum, and aluminum salt adjuvant approved for clinical use in humans, has been reported to selectively activate $T_z2$ cells in mice [Grun and Maurer, *Cell. Immunol.* 121:134–145 (1989)], while Freund's complete adjuvant (CFA), an emulsion of mineral oil with killed mycobacteria [Freund, et al., *Proc. Soc. Exp. Biol. Med.* 37:509 (1937)], preferentially activates murine $T_H1$ cells [Grun and Maurer, *Cell. Immunol.* 121:134–145 (1989)].

Another mechanism by which the immune response is augmented involves the direct stimulation of B cells by, for example, lipopolysaccharide (LPS) from Gram-negative bacteria. [Gery, et al., *J. Immunol.* 108:1088 (1972)]. LPS has also been shown to stimulate secretion of interferon-γ (INF-γ) [Tomai and Johnson, *J. Biol. Resp. Med.* 8:625–643 (1989)], which both inhibits proliferation of $T_H2$ cells and stimulates differentiation of $T_H1$ cells [Gajewski, et al., *J. Immunol.* 143:15–22 (1989); Gajewski, et al., *J. Immunol.* 146:1750–1758 (1991)]. The mechanism by which LPS potentiates the immune response is therefore through direct stimulation of B cells, and indirect regulation of both $T_H1$ and $T_H2$ cell populations.

Still other modes of immunopotentiation have been reported for other adjuvants. Oil emulsions (i.e., complete Freund's Adjuvant [CFA], Freund's incomplete adjuvant [FIA]) and liposomes act through depot formation as does alum, thus allowing for slow release of antigen. Slow release of antigen permits extended exposure of the antigen to the immune system and also allows for initial immunization with a dosage of antigen that, if delivered at one time, would ordinarily be counterproductive to antibody formation. It has been previously reported that while a large initial dose of antigen results in the production of a higher immediate titer of antibody, the increase in antibody titer and increase in antibody specificity as a function of time is not as great as observed with lower and more frequent doses of antigen [Siskind, G., *Pharm. Rev.* 25:319–324 (1973)]. Therefore, adjuvants which control presentation of an antigen to the immune system modulate antigen dosage in addition to altering the form, or complexity, of the antigen.

To date, only one adjuvant, alum [$AIK(SO_4)_2 \cdot H_2O$], has proven sufficiently non-toxic to permit its use in humans. Alum not only acts through $T_H2$ cell activation, depot formation and slow release of antigen following immunization [Edelman, *Rev. Infect. Dis.* 2:370–383 (1980); Warren, et al., *Ann. Rev. Immunol.* 4:369–388 (1986)], but also through granuloma formation by attracting immunocompetent cells [White, et al., *J. Exp. Med.* 102:73–82 (1955)] and activation of complement [Ramanathan, et al., *Immunol.* 37:881–888 (1979)]. However, alum is not without its negative side effects which include erythema, subcutaneous nodules, contact hypersensitivity, and granulomatous inflammation. Other adjuvants, which are widely employed outside of human application, are also the focus of continuing research to develop acceptable alternatives for use in humans. Included are the above mentioned oil emulsions (i.e., CFA and FIA), bacterial products (i.e., LPS, cholera toxin, mycobacterial components and whole killed *Corynebacterium parvum, Coyrnebacterium granulosum,* and *Bordetella pertussis,* liposomes, immunostimulating complexes (ISCOMs),and naturally occurring and derivatized polysaccharides from other than bacterial sources.

The immunopotentiating capacity of polysaccharides has been a focus of investigation over the past few years as these compounds are widespread in nature, e.g., as structural components in the cell walls of bacteria, and exoskeletons of insects and curstacea. Lipipolysaccharide (LPS) isolated from certain Gram-negative bacteria is one such polysaccharide even though the adjuvant properties of LPS are derived mainly from the lipid A region of the molecule, and not from the o-specific polysaccharide or core oligosccharide regions of the molecule. LPS, which augments both humoral [Johnson, et al., *J. Exp. Med.* 103:225–246 (1956)] and cell-mediated immunity [Ohta, et al., *Immunobiology* 53:827 (1984)], possesses numerous biological activities, but is impractical for use in humans due to its inherent toxicity as reviewed by Gupta, et al., *Vaccine* 11:291–306 (1993). Attention has therefore shifted to other polysaccharides including, among others, chitosan.

Chitosan [β-(1-4)-2-amino-2-deoxy-D-glucan] is a derivative of chitin and has been widely used in biomedical applications, due in part to is biodegradability by lysozyme and low toxicity in humans. These same properties have resulted in increased interest in chitosan as an immunopotentiating agent. For example, Matuhashi, et al., in U.S. Pat. No. 4,372,883, disclosed conjugation of soluble polysaccharides, including chitosan, to normally toxic antigens, conjugation thereby detoxifying the antigen and permitting its use as an immunogen. Matuhashi et al., however, did not address the use of insoluble forms of chitosan, nor did Matuhashi compare the resulting serum antibody titer with that obtained from immunization with other known adjuvants.

Likewise, Suzuki, et al., in U.S. Pat. No. 4,971,956, disclosed the use of water soluble chitosan-oligomers as therapeutics for treatment of bacterial and fungal infections, as well as for the treatment of tumers. Suzuki et al, discussed the difficulty in modifying chitosan to produce an appropriate water soluble form, disclosing that water-insoluble forms are impractical for therapeutic application. In addition, Suzuki et al., does not disclose conjugation of an antigen to chitosan to effect enhanced immune response.

Mitsuhashi, et al., in U.S. Pat. No. 4,814,169, disclosed the use of human protein conjugated to soluble polysaccharides, including chitosan, to generate antibodies against human protein in non-human animals. Administration of the human protein/polysaccharide solution was by intravenous, intraperitoneal, or subcutaneous injection. Other routes, including oral and rectal administration, were not addressed in the disclosure.

Nishimura, et al. [*Vaccine* 2:93–99 (1984)] reported the immunological properties of derivatives of chitin in terms of activation of peritoneal macrophages in vivo, suppression of tumor growth in mice, and protection against bacterial infection. Results suggested that both chitin and chitosan were ineffective stimulators of host resistance against challenge with tumor cells or bacteria, but that chitosan moderately induced cytotoxic macrophages. Results with modified, de-acetylated chitosan, which forms a gel in an aqueous environment, was shown to more effectively activate macrophages, suppress tumor growth and stimulate resistance to bacterial infection.

Marcinkiewica, et al., [*Arch. Immunol. Ther. Exp.* 39:127–132 (1991)] examined the immunoadjuvant activity of water-insoluble chitosan and reported significant enhancement of T-dependent humoral response, but only moderate augmentation of T-independent humoral response. The enhanced humoral response was detected with chitosan at doses of 100 mg/kg administered either intravenously or intraperitoneally. Subcutaneous and oral administration were specifically reported as being ineffective. In addition, Marcinkiewicz, et al., does not suggest conjugation of an antigen to insoluble chitosan, stating that chitosan "resulted in the same response irrespective of the site of administration—either together or separately from antigen."

In light of the fact that only one existing adjuvant has been approved for use in humans, there thus exists a need in the art to provide novel and less toxic adjuvants for potential application in humans. Improved adjuvants will permit the production of more effective vaccines and will improve the production of monoclonal antibodies with therapeutic potential.

SUMMARY OF THE INVENTION

In all of its aspects, the invention is directed to the use of chitosan formulations for potentiating an immune response in a host.

In one aspect, the present invention is directed to a method for potentiating an immune response comprising the steps of preparing a chitosan solution, incorporating an antigen into a phosphate buffer to form an antigen/phosphate buffer solution, lyophilizing the antigen/phosphate buffer solution to a lyophilized mixture, reconstituting the lyophilized mixture with the chitosan solution to form an antigen/chitosan mixture, and administering the mixture to an animal, including humans. The antigen/chitosan mixture may be administered to the animal via oral, rectal, intravaginal routes as well as via intraperitoneal injection, intramuscular injection, or subcutaneous injection; administration may comprise a single route or a multiplicity of routes.

In another aspect of the invention, a composition is provided which, comprises in combination lyophilized antigen/phosphate buffer and chitosan solution. The antigen/chitosan mixture may be administered to the animal via oral, rectal, intravaginal routes as well as via intraperitoneal injection, intramuscular injection, or subcutaneous injection; administration may comprise a single route or a multiplicity of routes.

Also provided by the invention is an immunogen comprising a lyophilized antigen/phosphate buffer and chitosan solution. The antigen/chitosan mixture may be administered to the animal via oral, rectal, intravaginal routes as well as via intraperitoneal injection, intramuscular injection, or subcutaneous injection; administration may comprise a single route or a multiplicity of routes.

In another aspect of the invention, a method is provided for preparing an immunogen comprising, preparing a chitosan solution, incorporating an antigen into a phosphate buffer to form an antigen/phosphate buffer solution, lyophilizing the antigen/phosphate buffer solution to a lyophilized mixture, and reconstituting the lyophilized mixture with the chitosan solution to form an antigen/chitosan mixture.

As another aspect of the invention, the present invention provides a method for potentiating an immune response comprising the steps of preparing a chitosan solution, preparing a sodium hydroxide solution, preparing an oil/surfactant solution, wherein the oil can be metabolically degraded, mixing the chitosan solution with the sodium hydroxide solution, the oil/surfactant solution, and the antigen to form an emulsion, and administering the emulsion to an animal. The antigen may be, but is not limited to, a protein, carbohydrate, lipid, glycoprotein or combinations thereof. Preferably the pH of the chitosan solution is about 5.0. The emulsion may be administered to the animal via intraperitoneal injection, intramuscular injection, or subcutaneous injection. The emulsion may also be administered alone, or in combination with any of a number of other adjuvants. Immunization may comprise a single administration or a multiplicity of administrations. In a more preferred embodiment, the oil is squalene.

In yet another aspect of the invention, a composition is provided which, when administered to an animal, will potentiate an immune response, the composition comprising antigen, sodium hydroxide, oil, surfactant, and chitosan solution, wherein the oil can be metabolically degraded.

Also provided by the invention is an immunogen comprising an antigen, sodium hydroxide solution, oil, surfactant, and a chitosan solution, wherein the oil can be metabolically degraded.

In another aspect of the invention, a method is provided for preparing an immunogen comprising, of preparing a chitosan solution, preparing a sodium hydroxide solution, preparing an oil/surfactant solution, wherein the oil can be metabolically degraded, mixing the chitosan solution with the sodium hydroxide solution, the oil/surfactant solution, and the antigen to form an emulsion.

Also provided in another aspect of the invention is a kit comprising a chitosan solution, a sodium hydroxide solution, and an oil/surfactant solution.

DETAILED DESCRIPTION OF THE INVENTION

The present invention is illustrated by the following examples relating to compositions and methods for using compositions for immunopotentiation which comprise an antigen/chitosan mixture or an antigen/chitosan/oil/surfactant emulsion, as well as methods to prepare the antigen/chitosan mixture and the antigen/chitosan/oil/surfactant emulsion. In particular Example 1 demonstrates the preparation of antigens incorporated and lyophilized in phosphate buffer, which is subsequently reconstituted in a chitosan solution. Example 2 provides a comparison of the ability of antigen incorporated into phosphate buffer and reconstituted in a chitosan solution to stimulate an immune response to that of a currently available adjuvant. Example 3 demonstrates the preparation of antigen incorporated in a chitosan/oil emulsion. Examples 4 and 5 provide a comparison of the ability of different antigens incorporated into a chitosan/oil emulsion to stimulate an immune response to that of a currently available adjuvant.

EXAMPLE 1

Preparation of Antigen Incorporated and Lyophilized in Phosphate Buffer and Reconstituted in Chitosan Solution While the following is exemplified by the use of chicken ovalbumin as an antigen, those of ordinary skill in the art will readily appreciate that any number of other antigens may be employed.

A 0.5M phosphate buffer was prepared by diluting 15.6 ml of phosphoric acid (16M; Mallinkrodt Chemical, Paris, Ky.) in 400 ml of deionized (18 mOhm: DI) water. The pH of the solution was adjusted to 7.3 with 10N sodium hydroxide (Sigma Chemical Co., St. Louis, Mo.). The total volume of the solution was adjusted to 500 ml by the addition of DI water.

A dilute chitosan solution was made by first preparing a 1% chitosan in 2% acetic acid solution: 1 gm of chitosan (practical grade; Sigma Chemical Co., St. Louis, Mo.) in 100 ml of 2% glacial acetic acid (Mallinkrodt Chemical, Paris, Ky.). The resulting 1% chitosan in 2% acetic acid solution was then diluted further by adding 7.4 ml of the solution to 2.6 ml of DI water to obtain a chitosan working solution. The pH of the final chitosan solution was between 4 and 5.

50 $\mu$L of a 10 mg/ml ovalbumin (Sigma Chemical Co., St. Louis, Mo.) solution in phosphate-buffered saline was added to a 10 ml vial containing 5 ml of the 0.5M phosphate buffer. This resulted in a clear flocculent. After adding 0.5 gm of d-sorbitol (Sigma Chemical Co., St. Louis, Mo.), the solution was rapidly frozen in liquid nitrogen and lyophilized.

Lyophilized sample was reconstituted with 5 ml of the working chitosan solution, mixed by vortex to form a cloudy solution containing white particles, and used for immunization as described in Example 2. The pH of the final solution was between 6 and 7.

EXAMPLE 2

Comparative Immunopotentiation with Antigen Incorporated and Lyophilized in Phosphate Buffer and Reconstituted in Chitosan Solution In order to determine the relative degree to which chisotsan potentiated the response to an antigen, a comparison (see Table 1) was undertaken between groups of mice that were previously immunized (individually) with either a vaccine comprising 25 $\mu$g of ovalbumin with CFA (Sigma Chemical Co., St. Louis, Mo.) or a vaccine comprising 25 $\mu$g of ovalbumin incorporated and lyophilized in phosphate buffer, and subsequently reconstituted in a chitosan solution (Test Group), as prepared in Example 1.

Female Balb/c mice, 8 weeks of age, were immunized by a single intraperitoneal injection of the vaccine on day 0. The ovalbumin CFA treatment group contained 3 mice, while the test group (treated ovalbumin incorporated and lyophilized in phosphate buffer and reconstituted in a chitosan solution) contained 4 mice. Both experimental groups were bled on day 7, post-injection. The CFA adjuvanted group was also bled on days 21, 28, 35, 42, and 48 post-immunization. The test group was also bled on days 26, 38, 38, 52, 70, 83, 102, 123, and 159 post-immunization. Anti-ovalbumin serum antibody titers were determined by ELISA.

TABLE 1

Comparative Immunopotentation with Antigen Incorporated and Lyophilized in Phosphate Buffer and Reconstituted in a Chitosan Solution (compilation of experiments)

| Day Post-Immunization | TEST GROUP (mean antibody titer) | CFA (mean antibody titer) |
|---|---|---|
| 7 | 1:100 | 1:73 |
| 21 | | 1:293 |
| 26 | 1:10,000 | |

TABLE 1-continued

Comparative Immunopotentation with Antigen Incorporated
and Lyophilized in Phosphate Buffer
and Reconstituted in a Chitosan Solution
(compilation of experiments)

| Day Post-Immunization | TEST GROUP (mean antibody titer) | CFA (mean antibody titer) |
| --- | --- | --- |
| 28 | | 1:3,200 |
| 35 | | 1:13,867 |
| 38 | 1:11,00 | |
| 42 | booster immunization administered (Test Group only) | 1:15,360 |
| 48 | | 1:20,480 |
| 52 | 1:64,000 | |
| 70 | 1:18,500 | |
| 83 | 1:10,250 | |
| 102 | 1:13,500 | |
| 123 | 1:10,000 | |
| 159 | 1:1750 | |

The results indicated that the composition comprising antigen incorporated and lyophilized in phosphate buffer and reconstituted in chitosan solution was apparently non-toxic to the recipient animals. The test group animals developed a high antibody titer by day 26 (10,000). The high titer persisted past 83 days post-immunization, via a booster vaccination on day 42. Immediately following the booster vaccination, the titer increased to approximately 64,000 (day 52) and persisted above 10,000 to approximately 123 days post-vaccination (original). The Test Group values obtained were comparable to those of the standard adjuvant used by those of ordinary skill in the art, complete Freud's Adjuvant. Further, the mean titer values in the test group animals were comparable to those seen with antigens cross-linked to chitosan with glutaraldehyde, which generally improves immunopotentiation over other commercially available adjuvants (PCT/US95/12189; WO 96/09805). In view of the unacceptability of glutaraldehyde in commercial vaccines and the present vaccine, wherein the antigen is administered in via incorporation and lyophilization in phosphate buffer and reconstituton in a chitosan solution, the present invention is a safe and comparable alternative adjuvant to both CFA and antigens cross-linked to chitosan via glutaraldehyde.

EXAMPLE 3

Preparation of an Antigen Incorporated into a Chitosan/Oil Emulsion

While the following is exemplified by the use of HIV-peptide-keyhole limpet hemocyanin conjugate (Example 4) or human zona pellucida B peptide-ovalbumin (Example 5) as antigens, those of ordinary skill in the art will readily appreciate that any number of other antigens may be employed. Further while the following is exemplified by the use of squalene, those of ordinary skill in the art will appreciate that any oil that is readily metabolized by the recipient animal may be used (e.g., corn, canola, peanut).

A 2% chitosan solution in 0.5M sodium acetate was prepared by dissolving 4.1 g of sodium acetate (Sigma Chemical Co., St. Louis, Mo.) in 50 ml of deionized (18 mOhm: DI) water with mixing. The pH of the solution was adjusted to 4.5 with approximately 7 ml of glacial acetic acid (Mallinkrodt Chemical, Paris, Ky.) and an additional 1.5 ml of glacial acetic acid was added to compensate for the effect of the addition of chitosan on the pH of the solution. The total volume of the solution was adjusted to 100 ml by the addition of DI water. 2 grams of chitosan (Sigma Chemical Co., St. Louis, Mo.) was slowly added to the sodium acetate solution with stirring and the mixture was stirred for 2–3 hours until the chitosan had dissolved. The chitosan solution was then sterilized by autoclaving during a 25 minute cycle. The solution was cooled to room temperature in a biosafety cabinet. The chitosan solution was then clarified by centrifugation in an IEC clinical centrifuge (International Equipment Co., Needham Hts., Mass.) at setting 7 for 5 minutes. The supernatant was decanted from the pellet (insoluble chitosan/chitin and contaminants). 87 to 90% (by weight) of the chitosan added was retained in the supernatant.

A 50% sodium hydroxide solution was prepared by dissolving 50 gm of sodium hydroxide (Sigma Chemical Co., St. Louis, Mo.) in 100 ml of deionized water, with mixing. A squalene/surfactant solution was prepared by combining 1500 $\mu$L of squalene (2,6,10,15,19,23-Hexamethyl-2,6,10, 14,18,22-tetracosahexaene; Sigma Chemical Co., St. Louis, Mo.) with 600 $\mu$L of the surfactant Pluronic® L121 (BASF Corp., Parisippany, N.J.) and vortexed until homogeneous.

A chitosan/squalene/surfactant/antigen emulsion was prepared by adding approximately 420 $\mu$L of antigen (i.e., HIV-peptide-keyhole limpet hemocyanin conjugate, Table 2; human zona pellucida B peptide-ovalbumin conjugates, Table 3) in water or urea to approximately 370 $\mu$L of 2% chitosan in 0.5M sodium acetate and vortexing. The actual amount of antigen (i.e., protein or peptide-carrier conjugate) used may range from 1 $\mu$g to several milligrams. 10 $\mu$L of the 50% sodium hydroxide were then added to the antigen/chitosan and the sample was vortexed. 10 $\mu$L aliquots of the 50% sodium hydroxide were added until a stable cloudy precipitate formed. Approximately 140 $\mu$L of the previously prepared squalene/surfactant solution was added to the above solutions of antigen & chitosan. The resulting solution was vortexed until a cloudy emulsion formed. Immediately prior to administration in the immunization studies as described in Examples 4 and 5, the resulting solution of chitosan/squalene/surfactant/antigen was mixed by vortex or syringe aspiration.

EXAMPLE 4

Comparative Immunopotentiation with Antigen (HIV-Peptide-KLH-Conjugate) Incorporated into a Chitosan/Squalene Emulsion The following experiments were conducted in order to asses the immune response to an antigen that has been incorporated into a chitosan/squalene emulsion. Specifically a comparative study was undertaken wherein groups of mice were individually immunized with either a vaccine comprising various amounts of HIV-peptide-KLH conjugate [Sarin et al., Vaccine Res., 3(1):49–57 (1994); incorporated herein by reference] with the chitosan/squalene/surfactant emulsion or 20 $\mu$g of HIV-peptide-KLH conjugate with CFA.

Referring to Tables 2 and 3, female, Balb/c mice, 8 weeks of age were immunized by a single 200 $\mu$L intraperitoneal injection of the vaccine on day 0. A second immunization was given to Group 1, at week 18 (126 days after the first immunization). A second immunization was administered to Groups 2 and 3 at week 24 (168 days after the first immunization). The second immunization consisted of the unconjugated HIV peptide at the dosage indicated with the chitosan/squalene/surfactant emulsion in Groups 1–3. The CFA group did not receive a second immunization. The subject animals were bled on days 22, 35, 49, 63, 77, 91, 119 (excluding Group 1), 140, and 149. Serum antibody titers were determined by ELISA.

TABLE 2

Immunization Groups in
Comparative Immunopotentiation Studies
with Chitosan/Squalene Emulsion

| Group # | µg of peptide | Adjuvant | No. of animals |
|---|---|---|---|
| 1 | 1 | chitosan/squalene | 8 |
| 2 | 3 | chitosan/squalene | 4 |
| 3 | 20 | chitosan/squalene | 4 |
| 4 | 20 | CFA | 4 |

TABLE 3

Comparative Immunopotentiation with Chitosan/Squalene Emulsion

| | Geometric mean antibody titer at week: | | | | | | | | |
|---|---|---|---|---|---|---|---|---|---|
| Grp # | 3 | 5 | 7 | 9 | 11 | 13 | 17 | 20 | 27 |
| 1 | 1:115 | 1:475 | 1:2260 | nd | 1:4000 | 1:2500 | nd | 1:35910 | nd |
| 2 | 1:126 | 1:6400 | 1:9190 | 1:11310 | 1:9120 | 1:1130 | 1:2000 | 1:707 | 1:18000 |
| 3 | 1:141 | 1:4500 | 1:18400 | 1:9500 | 1:12900 | 1:1900 | 1:3360 | 1:1680 | 1:9120 |
| 4 | 1:62 | 1:2600 | 1:3820 | 1:800 | 1:9120 | 1:3200 | 1:4700 | 1:2200 | nd | nd = not determined

The results indicated that the chitosan/squalene/surfactant emulsion adjuvant was apparently non-toxic to the recipient animals. The results also show that the Group 3 (20 µg peptide adjuvanted with chitosan/squalene/surfactant) performed as well as Group 4 (20 µg peptide adjuvanted with CFA), with an improved immune response in weeks 5 and 7 against the HIV-peptide-KLH conjugate. Further, Group 3 (3 µg peptide adjuvanted with chitosan/squalene/surfactant) produced results that were similar, if not better than Group 4 through week 11. Surprisingly, a second immunization with unconjugated peptide in groups receiving the chitosan/squalene emulsion resulted in a very strong boost response (see Group 1, post-week 18 and Groups 2–3, post-week 24). Overall the results set forth in Table 3 demonstrate that the chitosan/squalene emulsion induces a comparable, and in some cases better, humoral immune response than does CFA. Additionally, the chitosan/squalene/surfactant emulsion acted as an immunopotentiator as shown by a very strong boost response obtained with unconjugated HIV peptide.

EXAMPLE 4

Comparative Immunopotentiation with Antigen (Human Zona Pellucida B Peptide-Ovalbumin Conjugates) Incorporated into a Chitosan/Squalene Emulsion The following experiments were also conducted to asses the immune response to an antigen that has been incorporated into a chitosan/squalene/surfactant emulsion. Specifically a comparative study was undertaken wherein groups of mice were individually immunized (intraperitoneal) with a vaccine comprising 6 different human zona pellucida B (ZPB) synthetic peptides [SEQ ID NOS. 1–6] adjuvanted with either the chitosan/squalene/surfactant emulsion or CFA.

Female Balb/c mice, 8 weeks of female, were immunized by a 200 µL intraperitoneal injection of the vaccine (20 µg each of 6 different human ZPB synthetic peptides combine either with chitosan/squalene/surfactant emulsion (Group I) or CFA (Group II) on days 0 and 28. The Group II mice received CFA vaccine as the booster. Serum antibody titers were determined by ELISA using plates coated with 1 µg per well of a mixture of the 6 peptides. Antibody titers against full length purified recombinant human ZPB protein produced in Chinese hamster ovary cells [Harris et al. *J. Seq. and Mapping*, 4:361–393, 1994; incorporated herein by reference] were also determined by ELISA on plates coated with 50 ng of purified protein.

TABLE 4

Comparative Immunopotentiation with Chitosan/Squalene Emulsion
(data expressed as geometric mean)

| | Peptide specific antibody titers at day: | | | | Anti-CHO ZPB antibody titers at day: | | |
|---|---|---|---|---|---|---|---|
| Adjuvant | 21 | 43 | 60 | 81 | 43 | 60 | 81 |
| Group I | 1:4.47 | 1:30900 | 1:43700 | 1:87450 | 1:1350 | 1:2390 | 1:9120 |
| Group II | 1:9.45 | 1:8360 | 1:4550 | 1:11870 | 1:146 | 1:2.8 | 1:10 |

The results in Table 4 demonstrate that the animals immunized with the peptide-conjugate with chitosan/squalene/surfactant emulsion elicited a humoral response to both peptide and full-length protein superior to that elicited by immunization with peptide-conjugate adjuvanted with CFA.

Although the present invention has been described in terms of preferred embodiments, it is intended that the present invention encompass all modifications and variations which occur to those skilled in the art upon consideration of the disclosure herein, and in particular those embodiments which are within the broadest proper interpretation of the claims and their requirements.

What is claimed is:

1. A composition prepared by the process of:
   a) preparing a chitosan solution;
   b) incorporating an antigen into a phosphate buffer to form an antigen/phosphate buffer solution;
   c) lyophilizing the antigen/phosphate buffer solution to a lyophilized mixture; and
   d) reconstituting the lyophilized mixture in said chitosan solution to form an antigen/chitosan mixture.

2. The composition of claim 1 wherein the pH of the final solution is about 6.0 to about 7.0.

3. An immunogen prepared by the process of:
   a) preparing a chitosan solution;
   b) incorporating an antigen into a phosphate buffer to form an antigen/phosphate buffer solution;
   c) lyophilizing the antigen/phosphate buffer solution to a lyophilized mixture; and
   d) reconstituting the lyophilized mixture in said chitosan solution to form an antigen/chitosan mixture.

4. The immunogen of claim 3 wherein the pH of the final solution is about.

5. A method for producing an immunogen comprising the steps:
   a) preparing a chitosan solution;
   b) incorporating an antigen into a phosphate buffer;
   c) lyophilizing the antigen/phosphate buffer solution to a lyophilized mixture; and
   d) reconstituting the lyophilized mixture in said chitosan solution.

6. The method of claim 5 wherein the pH of the final solution is about 6.0 to about 7.0.

7. A method of potentiating an immune response in an animal comprising administering to the animal a composition according to claim 1 or claim 2.

* * * * *

UNITED STATES PATENT AND TRADEMARK OFFICE
CERTIFICATE OF CORRECTION

PATENT NO. : 5,965,144
DATED : October 12, 1999
INVENTOR(S) : Podolski et al.

It is certified that error appears in the above-identified patent and that said Letters Patent is hereby corrected as shown below.

<u>In the Claims</u>:

At column 14, line 2 of claim 4, immediately following "about" insert --6.0 to about 7.00--.

Signed and Sealed this

Sixth Day of March, 2001

Attest:

NICHOLAS P. GODICI

Attesting Officer     Acting Director of the United States Patent and Trademark Office